United States Patent [19]
Hanson et al.

[11] Patent Number: 5,739,016
[45] Date of Patent: Apr. 14, 1998

[54] ENZYMATIC HYDROLYSIS METHOD FOR THE PREPARATION OF C-13 HYDROXYL-BEARING TAXANES, AND USE THEREOF IN THE PREPARATION OF C-13 ACYLOXY-BEARING TAXANES

[75] Inventors: Ronald L. Hanson, Morris Plains; Ramesh N. Patel, Bridgewater; Laszlo J. Szarka, East Brunswick, all of N.J.

[73] Assignee: Bristol-Myers Squibb Company, Princeton, N.J.

[21] Appl. No.: 445,120

[22] Filed: May 19, 1995

Related U.S. Application Data

[62] Division of Ser. No. 77,979, Jun. 15, 1993, Pat. No. 5,516,676.

[51] Int. Cl.$^6$ .............................. C12P 17/02; C12N 9/14
[52] U.S. Cl. ......................... 435/117; 435/195; 435/123
[58] Field of Search ................................. 435/123, 117, 435/195

[56] References Cited

U.S. PATENT DOCUMENTS

| | | | |
|---|---|---|---|
| 4,010,072 | 3/1977 | Miura et al. | 435/195 |
| 4,017,362 | 4/1977 | Miura et al. | 435/195 |
| 4,067,774 | 1/1978 | Rubenstein et al. | 435/188 |
| 4,582,639 | 4/1986 | Matson et al. | 435/71 |
| 4,599,310 | 7/1986 | Matson et al. | 435/71 |
| 4,857,653 | 8/1989 | Colin et al. | 549/510 |
| 4,924,011 | 5/1990 | Denis et al. | 549/510 |
| 4,924,012 | 5/1990 | Colin et al. | 549/510 |
| 4,985,060 | 1/1991 | Higa | 435/195 |
| 5,202,448 | 4/1993 | Carver et al. | 435/117 |

FOREIGN PATENT DOCUMENTS

| | | |
|---|---|---|
| 0 253 739 | 1/1988 | European Pat. Off. . |
| 0 336 840 | 10/1989 | European Pat. Off. . |
| 0 336 841 | 10/1989 | European Pat. Off. . |
| PCT/US93/02193 | 9/1993 | WIPO . |
| WO 93/21338 | 10/1993 | WIPO . |

OTHER PUBLICATIONS

A. L. Lehninger, Biochemistry, 2nd Edition, Worth Pub. Inc., 1975, p. 256.

H. Prauser, Bergy's Manual of Systematic Bacteriology, Genus Nocardioides Prauser 1976,61$^{AL}$, vol. 4, 1989, pp. 2371–2375, S. T. Williams editor, Williams and Wilkins publ.

W. Boland, et al., Synthesis, "Esterolytic and Lipolytic Enzymes in Organic Synthesis", Dec., 1991, pp. 1049–1072.

E. Santaniello, et al., Chem. Rev., "The Biocatalytic Approach to the Preparation of Enantiomerically Pure Chiral Building Blocks", 1992, vol. 92, pp. 1071, 1094–1095.

I. Ringel et al., The Journal of Pharmacology and Experimental Therapeutics, "Taxol is Converted to 7–Epitaxol, a Biologically Active Isomer, in Cell Culture Medium", vol. 242, No. 2, pp. 692–698 (1987).

B. Monsarrat, et al., Drug Metabolism and Disposition, "Taxol Metabolism, Isolation and Identification of Three Major Metabolites of Taxol in Rat Bile", vol. 18, No. 6, pp. 895–901 (1990).

D. Kingston, Pharmac. Ther., "The Chemistry of Taxol", vol. 52, pp. 1–34, 1991.

G. Pedrocchi–Fantoni et al., J. Chem. Soc. Perkin Trans. 1, Regio– and Chemo–selective Properties of Lipase from Candida cylindracea, 1992, pp. 1029–1033.

V. S. Parmar, et al., Tetrahedron, "Regioselective Deacylation of Polyacetoxy Aryl–methyl Ketones by Lipases in Organic Solvents", vol. 48, No. 31, pp. 6495–6498, 1992.

M. Berger et al., Biotechnology Letters, "Regioselectivity of Lipases in Organic Solvents", vol. 13, No. 5, pp. 333–338 (1991).

R. Hanson et al., "Biotransformation of Taxus extracts with site–specific enzymes for hydrolysis of taxanes at C–10 and C–13", Biological Abstracts, xol. 97, 1994, Philadelphia, PA, US; abstract No. 206030, *abstract* 207th National Meeting of the American Chemical Society, San Diego, Mar. 13–17, 1994. Abstracts of Papers American Chemical Society 207 (1–2) 1994 Conference.

D. Cazzulino, et al., "Fermentation and Recovery of an Enzyme Used for Hydrolysis of Taxanes", Biological Abstracts, xol. 97, 1994, Philadelphia, PA, US; abstract No. 205977, *abstract* 207th National Meeting of the American Chemical Society, San Diego, Mar. 13–17, 1994. Abstracts of Papers American Chemical Society 207 (1–2) 1994 Conference.

Halarnkar, et al., "Formation of Cyclic Products from the Diepoxide of Long–Chain Fatty Esters by Cytosolic Epoxide Hydrolase", Archives of Biochemistry and Biophysics, vol. 294, No. 2, May 1, pp. 586–593, 1992.

Halarnkar, et al., "Catabolism of Epoxy Fatty Esters by the Purified Epoxide Hydrolase from Mouse and Human Liver", Archives of Biochemistry and Biophysics, vol. 272, No. 1, Jul., pp. 226–236, 1989.

Nourooz–Zadeh et al., "Characterization of the Cytosolic Epoxide Hydrolase–Catalyzed Hydration Products from 9,10:12,13–Diepoxy Stearic Esters", Archives of Biochemistry and Biophysics, vol. 294, No. 2, May 1, pp. 675–685, 1992.

*Primary Examiner*—Leon B. Lankford, Jr.
*Attorney, Agent, or Firm*—Suzanne E. Babajko

[57] ABSTRACT

An enzymatic hydrolysis method for the preparation of compounds useful as intermediates in the preparation of taxanes such as taxol, wherein one or more C-13 acyloxy-bearing taxanes are contacted with an enzyme or microorganism capable of hydrolyzing said acyloxy groups to hydroxyl groups.

10 Claims, No Drawings

ENZYMATIC HYDROLYSIS METHOD FOR THE PREPARATION OF C-13 HYDROXYL-BEARING TAXANES, AND USE THEREOF IN THE PREPARATION OF C-13 ACYLOXY-BEARING TAXANES

This is a division of application Ser. No. 08/077,979, filed Jun. 15, 1993, now U.S. Pat. No. 5,516,676.

FIELD OF THE INVENTION

The present invention relates to an enzymatic hydrolysis method for the preparation of C-13 hydroxyl-bearing taxanes useful as intermediates in the preparation of C-13 acyloxy-bearing taxanes, and particularly in the preparation of taxol and taxol analogues.

BACKGROUND OF THE INVENTION

Taxanes are diterpene compounds which find utility in the pharmaceutical field. For example, taxol, a taxane having the structure:

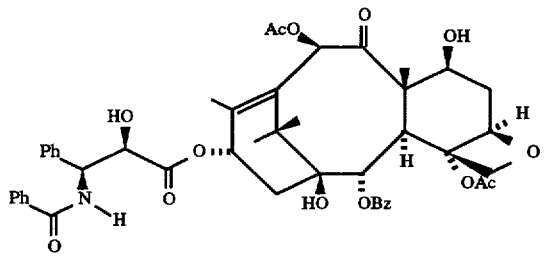

where Ph is phenyl, Ac is acetyl and Bz is benzoyl, has been found to be an effective anticancer agent.

Naturally occurring taxanes such as taxol may be found in plant materials, and have been isolated therefrom. Such taxanes may, however, be present in plant materials in relatively small amounts so that, in the case of taxol, for example, large numbers of the slow-growing yew trees forming a source for the compound may be required. The art has thus continued to search for synthetic, including semi-synthetic routes for the preparation of naturally occurring taxanes such as taxol, as well as for the preparation of analogues thereof.

Due to the complexity of the taxane ring structure, a taxane containing desired substituents on the ring system may more readily be prepared by the use of a starting material already having the basic taxane ring structure. Thus, for example, a compound having the taxane ring structure and containing a hydroxyl group at C-13 may be coupled with an intermediate compound to form a taxane having a desired sidechain at C-13, such as taxol.

SUMMARY OF THE INVENTION

The present invention provides a method for the preparation of C-13 hydroxyl-bearing taxane compounds, which compounds find utility as starting materials in the preparation of taxanes having a desired sidechain at C-13.

In particular, the present invention provides a method for the preparation of at least one taxane containing a hydroxyl group directly bonded at C-13, comprising the steps of contacting at least one taxane containing an acyloxy group directly bonded at C-13 with an enzyme or microorganism capable of catalyzing the hydrolysis of said acyloxy group to a hydroxyl group, and effecting said hydrolysis.

DETAILED DESCRIPTION OF THE INVENTION

The present invention provides an efficient method for the preparation of C-13 hydroxyl-bearing taxanes from C-13 acyloxy-bearing taxanes. A single taxane may be hydrolyzed, or a mixture of different taxanes may be sequentially or simultaneously hydrolyzed, according to the present invention. The present invention is described further as follows.

In a preferred embodiment, the present invention provides a method for the preparation of at least one C-13 hydroxyl-bearing taxane of the following formula I:

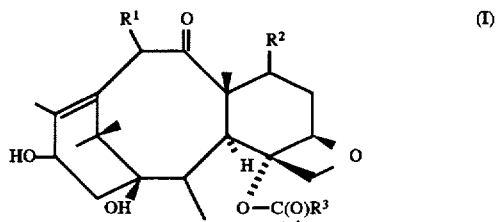

where
$R^1$ is hydrogen, hydroxyl, $R^5$—O—, $R^6$—C(O)—O—, or $R^6$—O—C(O)—O—;
$R^2$ is hydrogen, hydroxyl, fluoro, $R^5$—O—, xylosyl, $R^6$—C(O)—O— or $R^6$—O—C(O)—O—;
$R^3$ and $R^4$ are independently hydrogen, alkyl, alkenyl, alkynyl, cycloalkyl, cycloalkenyl, aryl, or heterocyclo;
$R^5$ is a hydroxyl protecting group; and
$R^6$ is hydrogen, alkyl, alkenyl, alkynyl, cycloalkyl, cycloalkenyl, aryl or heterocyclo,
or salts thereof,
comprising the steps of contacting at least one C-13 acyloxy-bearing taxane of the following formula II:

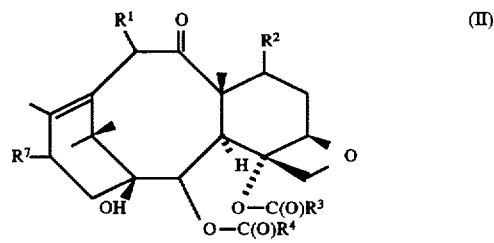

where
$R^1$, $R^2$, $R^3$ and $R^4$ are as defined above; and
$R^7$ is acyloxy,
or salts thereof,
with an enzyme or microorganism capable of catalyzing the hydrolysis of said $R^7$ acyloxy group to a hydroxyl group, and effecting said hydrolysis. All stereoconfigurations of the unspecified chiral centers of the compounds of the formulae I and II are contemplated in the method of the present invention, either alone (that is, substantially free of other stereoisomers) or in admixture with other stereoisomeric forms.

In another preferred embodiment, the present invention provides a method for the preparation of at least one first taxane, having a desired C-13 acyloxy sidechain, from at least one second taxane, having an undesired acyloxy C-13 sidechain, by enzymatic hydrolysis of the latter to provide at least one C-13 hydroxyl-containing analogue by the method described herein, followed by coupling of the desired sidechain thereto to provide the former. In this embodiment, the present invention provides, for example, a method for the preparation of a desired taxane, having a particular C-13 acyloxy sidechain, from a starting mixture of taxanes containing different acyloxy C-13 sidechains, which starting mixture may or may not include the desired taxane, by simultaneous or sequential hydrolysis of the different C-13 groups to provide one or more taxanes having a hydroxyl group at C-13, followed by coupling of the desired sidechain thereto. This preferred method is particularly useful where a mixture of taxanes having different C-13 acyloxy sidechains is obtained, such as by extraction of plant materials yielding taxol in admixture with cephalomannine and other naturally-produced taxanes, and where a particular taxane such as taxol is ultimately desired.

In the method of the present invention, the stereoconfiguration of the C-13 acyloxy group of the starting taxane is preferably retained in the C-13 hydroxyl group-containing product.

The terms "enzymatic process" or "enzymatic method", as used herein, denote a process or method of the present invention employing an enzyme or microorganism. The term "hydrolysis", as used herein, denotes the formation of a hydroxyl group from an acyloxy group, and may be achieved, for example, by contact with water and/or a suitable organic alcohol according to the method of the present invention. Use of "an enzyme or microorganism" in the present method includes use of two or more, as well as a single, enzyme or microorganism.

The terms "alkyl" or "alk", as used herein alone or as part of another group, denote optionally substituted, straight and branched chain saturated hydrocarbon groups, preferably having 1 to 12 carbons in the normal chain. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH).

The terms "lower alk" or "lower alkyl", as used herein alone or as part of another group, denote such optionally substituted groups as described above for alkyl having 1 to 4 carbon atoms in the normal chain.

The terms "alkoxy" or "alkylthio", as used herein alone or as part of another group, denote an alkyl group as described above bonded through an oxygen linkage (—O—) or a sulfur linkage (—S—), respectively. The term "alkyloxycarbonyl", as used herein alone or as part of another group, denotes an alkoxy group bonded through a carbonyl group. The term "alkylcarbonyloxy", as used herein alone or as part of another group, denotes an alkyl group bonded through a carbonyl group which is, in turn, bonded through an oxygen linkage. The terms "monoalkylamino" or "dialkylamino", as used herein alone or as part of another group, denote an amino group substituted by one or two alkyl groups as described above, respectively.

The term "alkenyl", as used herein alone or as part of another group, denotes such optionally substituted groups as described above for alkyl, further containing at least one carbon to carbon double bond. Exemplary substituents include one or more alkyl groups as described above, and/or one or more groups described above as alkyl substituents. The term "alkenyloxy", as used herein alone or as part of another group, denotes an alkenyl group as described above bonded through an oxygen linkage (—O—).

The term "alkynyl", as used herein alone or as part of another group, denotes such optionally substituted groups as described above for alkyl, further containing at least one carbon to carbon triple bond. Exemplary substituents include one or more alkyl groups as described above, and/or one or more groups described above as alkyl substituents. The term "alkynyloxy", as used herein alone or as part of another group, denotes an alkynyl group as described above bonded through an oxygen linkage (—O—).

The term "cycloalkyl", as used herein alone or as part of another group, denotes optionally substituted, saturated carbocyclic ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents. The term "cycloalkyloxy", as used herein alone or as part of another group, denotes a cycloalkyl group as described above bonded through an oxygen linkage (—O—).

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents. The term "cycloalkenyloxy", as used herein alone or as part of another group, denotes a cycloalkenyl group as described above bonded through an oxygen linkage (—O—).

The terms "ar" or "aryl", as used herein alone or as part of another group, denote optionally substituted, carbocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above and/or groups described above as alkyl substituents. The term "aryloxy", as used herein alone or as part of another group, denotes an aryl group as described above bonded through an oxygen linkage (—O—).

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. Exemplary substituents include one or more alkyl groups as described above and/or one or more groups described above as alkyl substituents. The term "heterocyclooxy", as used herein alone or as part of another group, denotes a heterocyclo group as described above bonded through an oxygen linkage (—O—).

The terms "halogen" or "halo", as used herein alone or as part of another group, denote chlorine, bromine, fluorine, and iodine.

The term "taxane", as used herein, denotes compounds containing a taxane moiety as described following. The term "taxane moiety", as used herein, denotes moieties containing the core structure (with numbering of ring system positions used herein shown):

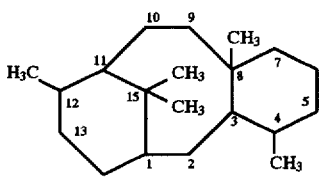

which core structure may be substituted and which may contain ethylenic unsaturation in the ring system thereof. Such moieties having an oxetane ring fused at the 4- and 5-positions, such as is found in taxol, are preferred.

The term "hydroxy (or hydroxyl) protecting group", as used herein, denotes any group capable of protecting a free hydroxyl group which, subsequent to the reaction for which it is employed, may be removed without disturbing the remainder of the molecule. Such groups, and the synthesis thereof, may be found in "Protective Groups in Organic Synthesis" by T. W. Greene, John Wiley and Sons, 1981, or Fieser & Fieser.

The term "salt", as used herein, includes acidic and/or basic salts formed with inorganic and/or organic acids and bases.

The term "acyl", as used herein alone or as part of another group, denotes the moiety formed by removal of the hydroxyl group from the group —COOH of an organic carboxylic acid. The term "acyloxy", as used herein alone or as part of another group, denotes an acyl group as described above bonded through an oxygen linkage (—O—).

Starting Materials

The C-13 acyloxy-bearing taxanes employed as starting materials for the present invention may be any such compounds capable of undergoing the enzymatic hydrolysis of the present invention. The starting materials may be synthetically formed taxanes, or preferably, naturally formed taxanes such as cephalomannine, 7-xylosyltaxol, taxol, 7-xylosyl-10-desacetyltaxol, 10-desacetyltaxol, or taxol C (an analogue of taxol wherein the benzoyl group of the C-13 taxol sidechain is replaced by an n-pentanoyl group), alone or in admixture with each other. The "naturally formed" taxane starting materials are preferably obtained by plant cell culture of, and/or extraction from, taxane-producing plant tissues, particularly tissues from, or derived from, plants of the *Taxus* genus such as *Taxus baccata*, *Taxus cuspidata*, *Taxus brevifolia*, *Taxus wallichiana*, *Taxus media*, *Taxus hicksii*, especially *Taxus x. media hicksii*. Exemplary plant tissues include the needles, bark and whole seedling.

For preferred methods of obtaining the C-13 acyloxy-bearing taxane starting materials of the present method see Rao, *Pharmaceutical Research*, 10, 521–524 (1993); Kingston, *Pharmac. Ther.*, 52, 1–34 (1991); or the Examples herein.

Enzymes and Microorganisms

The enzyme or microorganism employed in the present invention may be any enzyme or microorganism capable of catalyzing the enzymatic hydrolysis described herein. The enyzmatic or microbial materials, regardless of origin or purity, may be employed in the free state or immobilized on a support such as by physical adsorption or entrapment.

A preferred method for selecting a microorganism suitable for enzymatic hydrolysis of a starting C-13 acyloxy-bearing taxane according to the method of the present invention is by use of the following novel screening method, comprising the steps of:

(a) selecting a solid growth medium (i) in which the microorganism to be screened will grow, (ii) in which the starting C-13 acyloxy-bearing taxane is insoluble and thus, in admixture with the growth medium, has a cloudy appearance, and (iii) in which the C-13 hydroxyl-bearing taxane product of the hydrolysis method of the present invention is soluble, and, preferably, in which the cleaved C-13 sidechain is also soluble, and thus, in admixture with the growth medium, has a clear appearance;

(b) placing the microorganism into contact with the growth medium selected in step (a) above, for example, in a petri dish, into which the starting C-13 acyloxy-bearing taxane has been admixed, and under conditions allowing growth of the microorganism to occur; and (c) observing whether a clear zone appears around the area in which growth of the microorganism occurs.

The formation of a clear zone indicates that hydrolysis has occurred, and thus that the microorganism may be suitable for use in the present hydrolysis method. As used herein, the terms "clear" and "cloudy" are to be construed relative to each other. Thus, the starting C-13 acyloxy-bearing taxane is employed in admixture with the growth medium in sufficient quantity so as to be visible in suspension therein (giving a "cloudy" appearance), and clarity is determined relative to said initial degree of visibility in suspension, that is, as a lessening of that visibility.

Another preferred screening method provided by the present invention is that corresponding to the method set forth above, with the exception that a solid growth medium is selected in which the starting C-13 acyloxy-bearing taxane is soluble and thus, in admixture with the growth medium, has a clear appearance, while the C-13 hydroxyl-bearing taxane product of the hydrolysis method of the present invention is insoluble (and preferably in which the cleaved C-13 sidechain is also insoluble) and thus, in admixture with the growth medium, has a cloudy appearance. Observance of a cloudy zone around the area in which growth of the microorganism occurs allows selection of a suitable microorganism.

A particularly preferred embodiment of the screening method of the present invention is that set forth in the Examples herein.

The above preferred screening methods may suitably be employed where the starting C-13 acyloxy-bearing taxane and the C-13 hydroxyl-bearing taxane product differ in relative solubility to the extent that it may be observed whether or not hydrolysis according to the present invention has occurred.

Exemplary microorganisms include those within the following genera: *Nocardioides*, *Nocardia*, *Rhodococcus*, *Micropolyspora*, *Saccharopolyspora*, *Pseudonocardia*, *Oerskovia*, *Promicromonospora*, and *Intrasporangium*. Particularly preferred microorganisms are those species within the genus *Nocardioides*, such as *Nocardioides albus*, *Nocardioides flavus*, *Nocardioides fulvus*, *Nocardioides luteus*, *Nocardioides simplex*, and *Nocardioides thermolilacinus*, especially *Nocardioides albus* ATCC 55424 (SC 13910) and ATCC 55425 (SC 13911) and *Nocardioides luteus* ATCC 55426 (SC 13912). The term "ATCC" as used herein refers to the accession number of the American Type Culture Collection, 12301 Parklawn Drive, Rockville, Md. 20852, the depository for the organism referred to. The above microorganisms ATCC 55424, 55425 and 55426 were deposited on May 12, 1993. The term "SC" denotes the designation given to the microorganism as part of the Squibb culture collection.

The biologically pure microorganisms *Nocardioides albus* ATCC 55424 (SC 13910), *Nocardioides albus* ATCC 55425 (SC 13911), and *Nocardioides luteus* ATCC 55426 (SC 13912) are novel microorganisms further provided by the present invention. It should be understood that mutants of these organims are also contemplated by the present invention, for use in the hydrolysis methods described herein, such as those modified by the use of chemical, physical (for example, X-rays) or biological means (for example, by molecular biology techniques).

*Nocardioides albus* ATCC 55424 (SC 13910) and ATCC 55425 (SC 13911) may be cultivated on Medium A 94 (corn steep liquor (35 grams), Cerelose (20 grams), $(NH_4)_2SO_4$ Reagent Grade (5 grams), $CaCO_3$ (3.5 grams), soy bean oil (5 ml) and distilled water (1 liter)). These organisms were isolated from soil (from a sample from New Brunswick, N.J.), and are gram positive, non-motile organisms exhibiting aerobic growth on a variety of media. On solid YS medium (0.2% yeast extract, 1% starch), the mycelium is whitish to light cream colored. Growth is associated with production of a dark diffusible pigment in both solid and liquid media. Microscopically, growth in liquid culture is characterized by mycelial aggregates consisting of abundantly branching hyphae.

*Nocardioides luteus* ATCC 55426 (SC 13912) may be cultivated on Medium A 94 (corn steep liquor (35 grams), Cerelose (20 grams), $(NH_4)_2SO_4$ Reagent Grade (5 grams), $CaCO_3$ (3.5 grams), soy bean oil (5 ml) and distilled water (1 liter)). This organism was isolated from soil (from a sample from New Brunswick, N.J.), and is a gram positive, non-motile organism exhibiting aerobic growth on a variety of media. On solid YS medium (0.2% yeast extract, 1% starch), the mycelium is dark cream colored. Microscopically, growth in liquid culture is characterized by mycelial aggregates consisting of abundantly branching hyphae.

The organisms *Nocardioides albus* ATCC 55424 (SC 13910) and ATCC 55425 (SC 13911), and *Nocardioides luteus* ATCC 55426 (SC 13912), were identified as strains of *Nocardioides albus* and *Nocardioides luteus*, respectively, in accordance with the description given in *Bergey's Manual of Systematic Bacteriology*, Volume 2 (Ed. P. H. A. Sneath) (1986).

Exemplary enzymes for use in the present method are hydrolases. Preferred enzymes include those derived from microorganisms, particularly those microorganisms described above. Enzymes may be isolated, for example, by extraction and purification methods such as those described in the Examples herein, especially purification of the active fractions found extracellularly in the medium in which these organisms have been cultivated, such as by use of an anion exchange column, followed by hydrophobic interaction chromatography and gel filtration. The present invention further provides the enzymes capable of the present hydrolysis which may be isolated from *Nocardioides albus* ATCC 55424 (SC 13910) and ATCC 55425 (SC 13911), and *Nocardioides luteus* ATCC 55426 (SC 13912), for example, by the above techniques.

Where microorganisms are employed, the cells may be used in the form of intact wet cells or dried cells such as lyophilized, spray-dried or heat-dried cells, or in the form of treated cell material such as ruptured cells or cell extracts. The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic hydrolysis method of the present invention may be carried out subsequent to the fermentation of the microorganism (two-stage fermentation and hydrolysis), or concurrently therewith, that is, in the latter case, by in situ fermentation and hydrolysis (single-stage fermentation and hydrolysis).

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; and alcohols such as ethanol, propanol and the like.

Nitrogen sources may include N-Z amine A, corn steep liquor, soy bean meal, beef extracts, yeast extracts, molasses, baker's yeast, tryprone, nutrisoy, peptone, yeastamin, amino acids such as sodium glutamate and the like, sodium nitrate, ammonium sulfate and the like.

Trace elements may include magnesium, manganese, calcium, cobalt, nickel, iron, sodium and potassium salts. Phosphates may also be added in trace or, preferably, greater than trace amounts.

The medium employed may include more than one carbon or nitrogen source or other nutrient.

Preferred media for growth include aqueous media, particularly those described in the Examples herein.

The agitation and aeration of the reaction mixture affects the amount of oxygen available during the hydrolysis process when conducted, for example, in shake-flask cultures or fermentor tanks during growth of microorganisms. The agitation range from 100 to 250 RPM is preferred; aeration of about 1 to 10 volumes of air per volume of media per minute is preferred.

For growth of the microorganisms and/or hydrolysis according to the method of the present invention, the pH of the medium is preferably from about 6 to about 8.5, and the temperature is preferably from about 24° C. to about 37° C. Hydrolysis may, for example, be carried out in vitro over time periods such as 1 to 48 hours, or preferably until the yield of desired product is maximized. It is preferred to conduct the hydrolysis of the present invention at a pH of from 6 to 8, particularly under non-basic conditions.

It is also preferred to employ an aqueous liquid as the hydrolysis reaction medium, although an organic liquid, or a miscible or immiscible (biphasic) organic/aqueous liquid mixture, may also be employed. It is preferred to employ 0.025 to 0.25 weight % of the C-13 acyloxy-bearing taxane starting material(s) based on the combined weight of starting material(s) and hydrolysis reaction medium.

The amount of enzyme or microorganism employed relative to the starting material is selected to allow catalysis of the enzymatic hydrolysis of the present invention. It is preferred to obtain yields in excess of 90% (% C-13 hydrolyzed product obtained based on the starting acyloxy taxane) when employing the hydrolysis method of the present invention. Hydrolysis may be obtained selectively at C-13 of the starting taxane. That is, product(s) the greater portion (such as solely) of which are hydrolyzed at C-13 only may be obtained without hydrolysis at other positions.

Separation

The C-13 hydroxyl-bearing products of the process of the present invention, and coupled products such as those described below, may be isolated and purified, for example, by methods such as extraction, distillation, crystallization, and column chromatography.

Utility

Taxanes are diterpene compounds containing a taxane moiety as described above. Of particular interest are taxanes containing a taxane moiety in which the 11,12-positions are bonded through an ethylenic linkage, and in which the 13-position contains a sidechain, which taxanes are exemplified by taxol. Pharmacologically active taxanes such as taxol may be used as antitumor agents to treat patients suffering from cancers such as breast, ovarian, colon or lung cancers, melanoma and leukemia.

The C-13 hydroxyl containing compounds obtained by the hydrolysis method of the present invention are particularly useful as intermediates in the preparation of the aforementioned C-13 sidechain-bearing taxanes. In particular, the C-13 hydroxyl-bearing compounds prepared according to the present method may be coupled with sidechain-forming intermediate compounds, such as β-lactams, to obtain the C-13 sidechain-bearing taxanes. The addition of such a sidechain, in and of itself, may impart an increased or more desirable pharmacological activity to the taxane product, or may form a taxane product which is more readily converted to a taxane having an increased or more desirable pharmacological activity than the starting compound.

The C-13 hydroxyl-bearing compounds prepared according to the method of the present invention may optionally be modified prior to use in sidechain formation by coupling. For example, modification at C-10 according to U.S. patent application Ser. No. 08/077,980, entitled "Enymatic Hydrolysis Method for the Preparation of C-10 Hydroxyl-Bearing Taxanes and Enzymatic Esterification Method for the Preparation of C-10 Acyloxy-Bearing Taxanes", by Hanson et al., filed concurrently herewith (Attorney Docket No. LD59), incorporated herein by reference, may be conducted prior to, during, or subsequent to the hydrolysis method of the present invention; and/or one or more hydroxyl groups at positions other than C-13 may be protected prior to coupling and, thereafter, deprotected.

The C-13 hydroxyl-bearing taxanes obtained by the hydrolysis method of the present invention, optionally modified as above, may, for example, be used in the preparation of C-13 acyloxy sidechain-bearing taxanes such as those recited, and prepared by the methods described in, European Patent Publication No. 400,971, U.S. Pat. Nos. 4,876,399, 4,857,653, 4,814,470, 4,924,012, 4,924,011, and Kingston, *Pharm. Ther.*, Vol. 52, 1–34 (1991), especially U.S. patent application Ser. No. 07/995,443, filed Dec. 23, 1992 by Poss et al. (Attorney Docket No. LD60) and U.S. patent application Ser. No. 08/033,598, filed Mar. 19, 1993 by Thottathil et al. (Attorney Docket No. LD57), all incorporated herein by reference.

Preparation of C-13 acyloxy-bearing taxanes of the formula II is preferred.

Preferred Compounds

It is preferred to employ taxanes of the formula II or salts thereof in the method of the present invention, whereby enzymatic hydrolysis provides the corresponding compounds of the formula I or salts thereof. In formulae I and II, $R^1$ is preferably $R^6$—C(O)—O— such as acetyloxy, or hydroxyl; $R^2$ is preferably hydroxyl or xylosyl; $R^3$ is preferably alkyl such as methyl; $R^4$ is preferably aryl such as phenyl; and $R^7$ is preferably a group of the following formula III:

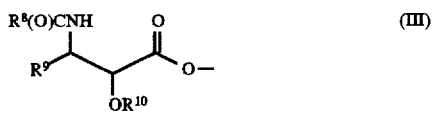

where
$R^8$ and $R^9$ are independently alkyl, alkoxy, alkenyl, alkenyloxy, alkynyl, alkynyloxy, cycloalkyl, cycloalkyloxy, cycloalkenyl, cycloalkenyloxy, aryl, aryloxy, heterocyclo or heterocyclooxy; and
$R^{10}$ is hydrogen or a hydroxyl protecting group.

Exemplary starting taxanes of the formula II are cephalomannine, 10-desacetyltaxol, 7-xylosyltaxol, taxol-C, and 7-xylosyl-10-desacetyltaxol, alone or in admixture with each other or taxol. Preferred hydrolysis products are baccatin III, 10-desacetylbaccatin III, 7-xylosylbaccatin III, and 7-xylosyl-10-desacetylbaccatin III.

Coupling subsequent to hydrolysis preferably provides taxane products of the formula II described above having C-13 acyloxy groups of the formula III. Taxol is preferably ultimately prepared by hydrolysis and coupling as described herein.

Salts or solvates such as hydrates of reactants or products may be employed or prepared as appropriate in any of the methods of the present invention.

The present invention is further described by the following examples which are illustrative only, and are in no way intended to limit the scope of the instant claims.

EXAMPLE 1

Selection of Strains of Microorganisms Capable of Removing the C-13 Sidechain of Taxol Difco spirit blue agar medium (5.25 g) in 150 ml distilled water was sterilized and partially cooled according to the manufacturer's instructions. The medium contained 10 g tryptone, 5 g yeast extract, 20 g agar, and 0.15 g spirit blue per liter. 25 mg taxol and 10 μl Tween 80 in 1 ml methanol were added to the medium through a sterile filter. 15 ml medium were used per 100 mm×15 mm petri dish.

After the plates had cooled and dried, soil samples were plated out as follows. 2 g soil was suspended in 40 ml water. A sample of the suspension was diluted 100-fold with water and 0.1 ml was spread per plate. The water used had been filtered through a 0.22μ filter. Plates were incubated at 28° C., and colonies surrounded by a cleared zone were selected. The basis for the selection was that taxol is insoluble at the concentration used in the medium, giving the plates a cloudy appearance, whereas baccatin III and the side chain produced by hydrolysis are soluble, thereby forming a clear zone around the colonies. The microorganisms selected include: *Nocardioides albus* strains ATCC 55424 (SC 13910) and ATCC 55425 (SC 13911); and *Nocardioides luteus* strain ATCC 55426 (SC 13912).

EXAMPLE 2

Removal of C-13 Sidechain from Taxol

The reaction of this Example proceeded as set forth in Scheme 1 following. 50 ml Erlenmeyer flasks containing 10 ml medium were inoculated with *Nocardioides albus* strains ATCC 55424 (SC 13910) or ATCC 55425 (SC 13911) isolated from soil as described in Example 1 and shaken for two days at 28° C., 150 RPM. The medium contained per liter distilled water: 10 g Bacto tryprone, 5 g Bacto yeast extract and 0.06 ml Tween 80 at pH 6.8±0.2. Cells were removed by centrifugation and the pH of the supernatants was adjusted from 8.66 to 7 with 1M $KH_2PO_4$.

0.5 mg taxol in 20 µl methanol was added to 2 ml of each supernatant and the mixtures were stirred for 21 hours at ambient temperature (about 23° C.). The solutions were extracted with 4 ml $CH_2Cl_2$. Extracts were dried under $N_2$ at room temperature, redissolved in methanol and analyzed by HPLC (Method 1 described following). Supernatant from strain ATCC 55424 (SC 13910) gave 0.008 mg/ml taxol and 0.163 mg/ml baccatin III (94.9 mol % conversion). Supernatant from strain ATCC 55425 (SC 13911) gave 0.014 mg/ml taxol and 0.166 mg/ml baccatin III (96.7 mol % conversion). (Baccatin III and the cleaved side chain product were identified by LC-MS).

Scheme 1

TAXOL

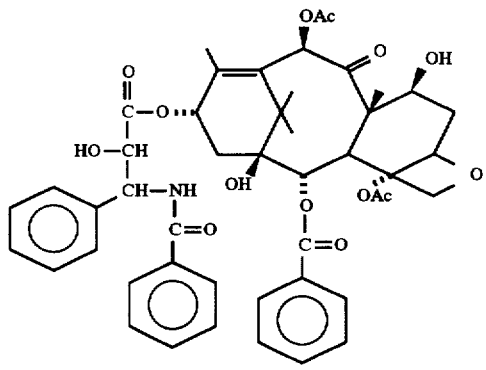

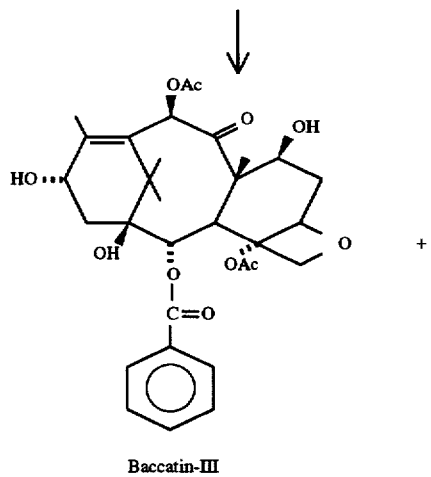

Baccatin-III

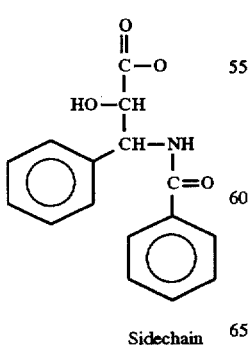

Sidechain

EXAMPLE 3

Removal of C-13 sidechain from Cephalomannine

Two 50 ml Erlenmeyer flasks each containing 10 ml medium (35 g corn steep liquor, 20 g cerelose, 5 g $(NH_4)_2SO_4$, 3.5 g $CaCO_3$, and 5 ml soybean oil brought to 1 liter with distilled water) were each inoculated with 0.5 ml *Nocardiodes albus* strain ATCC 55425 (SC 13911). After two days incubation at 28° C., 150 RPM, these two cultures were added to a 4 L flask containing 1 L of the medium used in Example 2. After 72 hours at 28° C., 200 RPM, cells were removed by centrifugation and the supernatant was adjusted from pH 8.16 to pH 7 with 1M $KH_2PO_4$.

0.5 mg cephalomannine in 20 µl methanol was incubated with 2 ml supernatant for 17 hours on an end-over-end shaker (Fisher Roto-Rack). The solution was extracted with methylene chloride, the extract was evaporated, resuspended in methanol and analyzed by HPLC (Method 2 described following). Cephalomannine concentration was decreased from 0.175 mg/ml to 0 and 0.110 mg/ml baccatin III was produced (89 mol % yield based on analyzed initial cephalomannine concentration).

EXAMPLE 4

Removal of C-13 Sidechain from 7-Xylosyltaxol

Enzymes from *Nocardiodes albus* strains ATCC 55424 (SC 13910) and ATCC 55425 (SC 13911) were prepared as described in Example 3, except that 1 L cultures were incubated for two days instead of three. *Nocardioides luteus* strain ATCC 55426 (SC 13912) was grown as described for *Nocardiodes albus* strain ATCC 55425 (SC 13911) in Example 3. After three days, cells were harvested by centrifugation, washed with 600 ml 50 mM potassium phosphate buffer pH 7 an6 centrifuged again. 36.6 g wet cells were frozen at -72° C., lyophilized to 2.52 g in two days, ground with a mortar and pestle, and stored at 2° C.

1.8 ml supernatant from strains ATCC 55424 (SC 13910) and ATCC 55425 (SC 13911), and 50 mg dried cells of strain ATCC 55426 (SC 13912) in 1.8 ml water were each incubated with 0.5 mg 7-xylosyltaxol in 0.2 ml methanol for 42 hours at room temperature on a Fisher Roto-Rack. The reactions were extracted with methylene chloride, and the dried extracts were dissolved in methanol for HPLC analysis (Method 1 described following). 7-Xylosyltaxol decreased from 0.218 mg/ml to 0 with each enzyme. The major product in each sample was identified as 7-xylosylbaccatin III by HPLC—mass spectrometry. Based on a baccatin III standard, ATCC 55424 (SC 13910), ATCC 55425 (SC 13911), and ATCC 55426 (SC 13912) gave 7-xylosylbaccatin III product concentrations of 0.112, 0.118, and 0.120 mg/ml, respectively. Using the same extinction coefficient at 235 nm for baccatin III and 7-xylosylbaccatin III, the calculated yields would be 88%, 93%, and 94%, respectively (molar % s).

EXAMPLE 5

Hydrolysis of Plant Cell Mixtures 1 g *Taxus hicksii* needles was extracted with 10 ml methanol:acetic acid 5000:1. To 10 ml extract was added 10 ml water:acetic acid 500:1. The mixture was centrifuged for 10 minutes at 48,000×g and 20° C. The pellet was discarded. 4 ml extract and 16 ml supernatant from *Nocardioides albus* strain ATCC 55424 (SC 13910) or ATCC 55425 (SC 13911) (prepared as described in Example 4) were shaken in a 50 ml Erlenmeyer flask at 28° C., 150 RPM for 42 hours. Samples were extracted with methylene chloride and the evaporated extracts were dissolved in methanol for analysis by HPLC (Method 2 described following). The taxane concentrations and molar ratios of (baccatin III+10-desacetylbaccatin III)/ initial taxol, with and without enzyme treatment, are shown in the following Table 1.

TABLE 1

Enzymatic Hydrolysis of Needle Extract

| Enzyme from+ | 10-des-acetyl-baccatin III µg/ml | baccatin III µg/ml | 7-xylosyl-10-des-acetyltax-ol µg/ml | cephalo-mannine µg/ml | taxol µg/ml | (DAB + B)* (taxol) |
|---|---|---|---|---|---|---|
| None | 0.126 | trace | 0.012 | 0.153 | 0.392 | 50.4 |
| SC13910 | 0.602 | 0.319 | 0.000 | 0.000 | 0.000 | 359.3 |
| SC13911 | 0.959 | 0.294 | 0.000 | 0.000 | 0.000 | 492.8 |

*Values given in molar % (DAB + B) ÷ (initial taxol);
DAB = 10-desacetylbaccatin III
B = baccatin III HPLC Methods Method 1[1/]

Column: Hewlett Packard hypersil 5 micron ODS C18 200×4.6 mm
Mobile phase: 60% methanol, 40% water
Flow rate: 1 ml/min
Column temperature: ambient
Detection wavelength: 235 nm Method 2

Column: Phase Separations Inc. (Norwalk, Conn.) microbore spherisorb phenyl 150×2.0 mm, 3 micron
Mobile phase: Solvent A:15 mM $KH_2PO_4$ adjusted to pH 4 with trifluoroacetic acid. Solvent B: acetonitrile.

| Time (Minutes) | Solvent A (%) | Solvent B (%) |
|---|---|---|
| 0 | 75 | 25 |
| 20 | 55 | 45 |
| 23 | 40 | 60 |
| 24 | 25 | 75 |
| 28 | 75 | 25 |

Column temperature: 35° C.
Detection wavelength: 230 nm

[1/] Monsarrat et al., Drug Metabolism and Disposition, 18, 895–901 (1990).

EXAMPLE 6

Purification of Enzyme and Hydrolysis of Taxanes 100 ml medium (35 g corn steep liquor, 20 g cerelose, 5 g ammonium sulfate, 3.5 g calcium carbonate, and 5 ml soybean oil brought to 1 liter with distilled water) in a 500 ml Erlenmeyer flask was inoculated with 1 ml Nocardioides albus ATCC 55425 (SC 13911) in the same medium and shaken for 2 days at 28° C. 20 ml of this culture was transferred to 1 L distilled water containing 10 g tryptone and 5 g yeast extract, pH 6.8±0.2 in a 4 L Erlenmeyer flask. The flask was shaken for 3 days at 28° C., cells were removed by centrifugation and the supernatant was adjusted from DH 7.89 to pH 7 with 1M $KH_2PO_4$.

All purification steps were performed at 4° C. The supernatant was applied to 150 ml Whatman DE52 anion exchanger in 25 mM potassium phosphate buffer pH 7 in a 5 cm diameter column. The column was washed with 150 ml buffer, then 450 ml buffer containing 0.25M NaCl. Enzyme activity was eluted with buffer plus 0.45M NaCl. The flow rate was 5 ml/min. Ammonium sulfate (100 mg/ml) was added to the most active fractions from the DE52 column, and the solution was applied to 30 ml Pharmacia Phenyl Sepharose CL-4B (hydrophobic interaction chromatography) in 50 mM potassium phosphate buffer pH 7 containing 100 mg/ml ammonium sulfate in a 2.6 cm diameter column at a flow rate of 1.6 ml/min. The column was washed with 150 ml buffer plus 20 mg/ml ammonium sulfate, then activity was eluted with buffer alone. The most active fractions from the Phenyl Sepharose column were concentrated by ultrafiltration to 4 ml using an Amicon YM10 membrane and passed through a Pharmacia Sephacryl S-200 gel filtration column (2.6×84 cm) at a flow rate of 0.65 ml/min. The fraction of highest specific activity had a single band of molecular weight 49,000±10,000 on a sodium dodecyl sulfate (SDS) gel. The purification is summarized in Table 2 following. (1 milliunit enzyme (mu) catalyzes the conversion of 1 nmole/min of taxol to baccatin-III at 28° C. in 50 mM potassium phosphate buffer containing 0.25 mg/ml taxol and 1% methanol.)

TABLE 2

| Step | Volume ml | Protein mg | Activity mu |
|---|---|---|---|
| medium | 1000 | 885 | 4664 |
| DE52 | 99 | 104 | 1194 |
| Phenyl Sepharose CL-4B | 16 | 6.45 | 801 |
| Sephacryl S-200 | 8.8 | 0.150 | 164 |

| Step | Specific Activity mu/mg | Recovery % |
|---|---|---|
| medium | 5.27 | |
| DE52 | 11.5 | 25.6 |
| Phenyl Sepharose CL-4B | 124 | 17.2 |
| Sephacryl S-200 | 1093 | 3.5 |

To demonstrate the activity of the enzyme purified above, the following experiments were conducted employing the taxane substrates listed in Table 3.

Samples were prepared containing 0.5 mg taxane substrate and 1% methanol in 2.0 ml 50 mM potassium phosphate buffer, pH 7 (Samples 1, 2, 3, 4 and 5). Samples were also prepared containing 10 mu enzyme of the enzyme purified through the Phenyl Sepharose CL-4B step described above in addition to 0.5 mg taxane substrate and 1% methanol in 2.0 ml 50 mM potassium phosphate buffer, pH 7 (Samples 1e, 2e, 3e, 4e and 5e). All samples were mixed for 16 hours with a Fisher Roto Rack at 28° C. Samples 1, 1e, 2, 2e, 5 and 5e were extracted with 4 ml methylene chloride. 2 ml of the extract were dried, redissolved in 1 ml methanol and analyzed by HPLC Method 1. Samples 3, 3e, 4 and 4e were diluted with 2 ml methanol and analyzed by HPLC Method 1 (C-13 sidechain was measured in these latter samples only).

Table 3 shows the amount of taxane substrate (mg/ml) remaining in each of the samples after incubation, as well as the amount of product taxane (mg/ml) present at the end of the incubation. As can be seen from Table 3 (see Samples 1e, 2e, 3e, 4e and 5e), the enzyme purified as above is effective in removing the C-13 side chain by hydrolysis of the taxane substrates listed therein.

TABLE 3

Hydrolysis of Taxanes by Purified Enzyme

| Sample | Substrate | Remaining mg/ml | Product | mg/ml | Side chain mg/ml |
|---|---|---|---|---|---|
| 1 | taxol | 0.268 | | 0.003 | |
| 1e | | 0.030 | baccatin-III | 0.170 | |
| 2 | cephalomannine | 0.239 | | | |
| 2e | | 0.011 | baccatin-III | 0.190 | |
| 3 | 7-xylosyltaxol | 0.250 | | | |
| 3e | | 0.016 | 7-xylosylbaccatin-III | 0.182 | 0.066 |
| 4 | 7-xylosyl-10-deacetyltaxol | 0.250 | | | |
| 4e | | 0.113 | 7-xylosyl-10-deacetylbaccatin-III | 0.108 | 0.044 |
| 5 | 10-deacetyl-taxol | 0.257 | | | |
| 5e | | 0.000 | 10-deacetyl baccatin-III | 0.150 | |

EXAMPLE 7

Hydrolysis of Seedling Extract

An ethanol extract of *Taxus hicksii* seedlings was concentrated 10- to 15-fold with nanofilters. 0.5 ml extract, 0.5 ml 1M potassium phosphate buffer DH 7, 54 mu partially purified enzyme from *Nocardioides albus* ATCC 55425 (SC 13911) (see Example 6 above) and 4 ml water were mixed at 28° C. for 48 hours on a Fisher Roto Rack. A control sample received no enzyme. Samples were extracted with methylene chloride and the evaporated extracts were dissolved in methanol for analysis by HPLC Method 2. The results obtained are shown in the following Table 4.

TABLE 4

Hydrolysis of Seedling Extract

| Enzyme from | 10-DAB mg/ml | bacc-III mg/ml | ceph mg/ml | XDT mg/ml | taxol mg/ml |
|---|---|---|---|---|---|
| none | 0.167 | 0.142 | 0.243 | 0.246 | 0.401 |
| SC13911 | 0.400 | 0.771 | 0.000 | 0.027 | 0.000 |

| Enzyme from | 10-DAT mg/ml | taxol C mg/ml | (DAB + B)/ (initial taxol) mol % yield |
|---|---|---|---|
| none | 0.201 | trace | 116.8 |
| SC13911 | 0.014 | 0.000 | 436.3 |

In Table 4: 10-DAB is 10-desacetylbaccatin III
bacc-III or B is baccatin III
ceph is cephalomannine
XDT is 7-xylosyl-10-desacetyltaxol
10-DAT is 10-desacetyltaxol

What is claimed is:

1. A method for the preparation of at least one taxane containing a hydroxyl group directly bonded at C-13, comprising the steps of contacting at least one taxane containing an acyloxy group directly bonded at C-13 with an enzyme derived from a microorganism selected from the group consisting of *Nocardioides albus* and *Nocardioides luteus* or with a microorganism selected from the group consisting of *Nocardioides albus* and *Nocardioides luteus*, wherein said enzyme or microorganism is capable of catalyzing the hydrolysis of said acyloxy group to a hydroxyl group, and effecting said hydrolysis.

2. The method of claim 1, wherein at least one C-13 hydroxyl-bearing taxane of the following formula I is prepared:

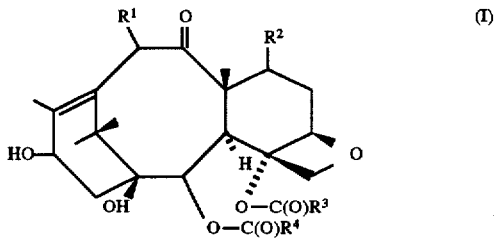

where
$R^1$ is hydrogen, hydroxyl, $R^5$—O—, $R^6$—C(O)—O—, or $R^6$—O—C(O)—O—;
$R^2$ is hydrogen, hydroxyl, fluoro, $R^5$—O—, xylosyl, $R^6$—C(O)—O— or $R^6$—O—C(O)—O—;
$R^3$ and $R^4$ are independently hydrogen, alkyl, alkenyl, alkynyl, cycloalkyl, cycloalkenyl, aryl, or heterocyclo;
$R^5$ is a hydroxyl protecting group; and
$R^6$ is hydrogen, alkyl, alkenyl, alkynyl, cycloalkyl, cycloalkenyl, aryl or heterocyclo,
or a salt thereof,
by contacting at least one C-13 acyloxy-bearing taxane of the following formula II:

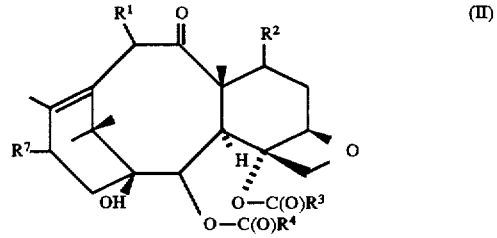

where
$R^1$, $R^2$, $R^3$ and $R^4$ are as defined above; and
$R^7$ is acyloxy,
or a salt thereof,
with said enzyme or microorganism.

3. The method of claim 2, wherein said taxane of the formula II is cephalomannine, 7-xylosyl-10-desacetyltaxol, 10-desacetyltaxol, 7-xylosyltaxol, taxol-C, and/or taxol, and said taxane of the formula I is baccatin III, 10-desacetylbaccatin III, 7-xylosyl-10-desacetylbaccatin III and/or 7-xylosylbaccatin III.

4. The method of claim 2, wherein the acyloxy-bearing taxane starting material employed in said hydrolysis method comprises a mixture of acyloxy-bearing taxanes having different sidechains at C-13.

5. The method of claim 4, wherein said mixture of taxanes is obtained by plant cell culture of, and/or extraction from, plant tissue, wherein said plant is a member of the *Taxus* genus.

6. The method of claim 1, wherein said microorganism is selected from the group consisting of *Nocardioides albus* ATCC 55424 (SC 13910), *Nocardioides albus* ATCC 55425 (SC 13911), and *Nocardioides luteus* ATCC 55426 (SC 13912).

7. The method of claim 1, wherein said enzyme is a hydrolase.

8. The method of claim 1, wherein said enzyme is derived from a microorganism selected from the group consisting of *Nocardioides albus* ATCC 55424 (SC 13910), *Nocardioides*

*albus* ATCC 55425 (SC 13911), and *Nocardioides luteus* ATCC 55426 (SC 13912).

9. The method of claim 1, wherein, subsequent to said hydrolysis, said at least one taxane containing a hydroxyl group directly bonded at C-13, in which hydroxyl groups at positions other than C-13 are optionally protected, is coupled with a compound forming an acyloxy sidechain at C-13.

10. The method of claim 9, wherein taxol is ultimately prepared by said method comprising hydrolysis and coupling.

* * * * *